(12) United States Patent
Stopek et al.

(10) Patent No.: US 7,923,439 B2
(45) Date of Patent: Apr. 12, 2011

(54) HYDROXAMATE COMPOSITIONS

(75) Inventors: Joshua Stopek, Yalesville, CT (US); Ahmad Hadba, Middlefield, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 4 days.

(21) Appl. No.: 12/573,232

(22) Filed: Oct. 5, 2009

(65) Prior Publication Data

US 2010/0093846 A1 Apr. 15, 2010

Related U.S. Application Data

(60) Provisional application No. 61/105,478, filed on Oct. 15, 2008.

(51) Int. Cl.
| | |
|---|---|
| A61K 31/66 | (2006.01) |
| A61K 31/34 | (2006.01) |
| A61K 31/16 | (2006.01) |
| A61K 31/13 | (2006.01) |
| A61F 13/00 | (2006.01) |
| A61F 2/00 | (2006.01) |

(52) U.S. Cl. ........ 514/114; 514/473; 514/613; 514/645; 424/422; 424/423; 424/427; 424/443

(58) Field of Classification Search .................. 514/114, 514/473, 613, 645; 424/422, 423, 427, 443
See application file for complete search history.

(56) References Cited

U.S. PATENT DOCUMENTS

| | | | |
|---|---|---|---|
| 3,187,752 A | 6/1965 | Glick |
| 3,565,077 A | 2/1971 | Glick |
| 4,014,973 A | 3/1977 | Thompson |
| 4,027,676 A | 6/1977 | Mattei |
| 4,043,344 A | 8/1977 | Landi et al. |
| 4,047,533 A | 9/1977 | Perciaccante et al. |
| 4,190,720 A | 2/1980 | Shalaby |
| 4,201,216 A | 5/1980 | Mattei |
| 4,582,052 A | 4/1986 | Dunn et al. |
| 4,605,730 A | 8/1986 | Shalaby et al. |
| 4,624,256 A | 11/1986 | Messier et al. |
| 4,700,704 A | 10/1987 | Jamiolkowski et al. |
| 4,705,820 A | 11/1987 | Wang et al. |
| 4,711,241 A | 12/1987 | Lehmann |
| 4,788,979 A | 12/1988 | Jerrett et al. |
| 4,791,929 A | 12/1988 | Jerrett et al. |
| 4,994,074 A | 2/1991 | Bezwada et al. |
| 5,019,093 A | 5/1991 | Kaplan et al. |
| 5,032,638 A | 7/1991 | Wang et al. |
| 5,047,048 A | 9/1991 | Bezwada et al. |
| 5,059,213 A | 10/1991 | Chesterfield et al. |
| 5,100,433 A | 3/1992 | Bezwada et al. |
| 5,133,738 A | 7/1992 | Korthoff et al. |
| 5,133,739 A | 7/1992 | Bezwada et al. |
| 5,181,923 A | 1/1993 | Chesterfield et al. |
| 5,226,912 A | 7/1993 | Kaplan et al. |
| 5,261,886 A | 11/1993 | Chesterfield et al. |
| 5,306,289 A | 4/1994 | Kaplan et al. |
| 5,318,575 A | 6/1994 | Chesterfield et al. |
| 5,352,515 A | 10/1994 | Jarrett et al. |
| 5,370,031 A | 12/1994 | Koyfman et al. |
| 5,383,387 A | 1/1995 | Chesterfield et al. |
| 5,662,682 A | 9/1997 | Chesterfield et al. |
| 5,667,528 A | 9/1997 | Colligan |
| 5,716,376 A | 2/1998 | Roby et al. |
| 6,177,094 B1 | 1/2001 | Jiang |
| 6,203,564 B1 | 3/2001 | Hutton et al. |
| 2004/0213758 A1 | 10/2004 | Sefton et al. |
| 2007/0104678 A1 | 5/2007 | May et al. |
| 2007/0160655 A1 | 7/2007 | Sefton et al. |

FOREIGN PATENT DOCUMENTS

| | | |
|---|---|---|
| EP | 1669093 A1 | 6/2006 |
| EP | 2028208 A1 | 2/2009 |
| FR | 2630728 A1 | 11/1989 |
| WO | WO01/30795 A1 | 5/2001 |
| WO | WO2006/002050 A1 | 1/2006 |
| WO | WO2006/002506 | 1/2006 |
| WO | WO2006/133569 | 12/2006 |
| WO | WO2008/143654 A1 | 11/2008 |
| WO | WO2008/144247 A1 | 11/2008 |
| WO | WO2008/144248 A1 | 11/2008 |

OTHER PUBLICATIONS

European Search Report for EP 09252411.5-1214 date of completion is Jan. 22, 2010 (4 pages).

*Primary Examiner* — Raymond J Henley, III

(57) ABSTRACT

The present disclosure provides compositions including a first component including at least one phospholipid possessing at least one vinyl group, a second component including a furanone possessing vinyl and/or acrylate groups, and a third component including a hydroxamate. Compositions, medical devices, and coatings including copolymers and blends of the foregoing components are also provided.

20 Claims, No Drawings

HYDROXAMATE COMPOSITIONS

CROSS-REFERENCE TO RELATED APPLICATIONS

This application claims the benefit of and priority to U.S. Provisional Application Ser. No. 61/105,478, filed Oct. 15, 2008, the entire disclosure of which is incorporated by reference herein.

TECHNICAL FIELD

The present disclosure relates to compositions including copolymers possessing furanones in combination with hydroxamates, and articles made from or coated with such copolymers or compositions.

BACKGROUND OF RELATED ART

Matrix metalloproteinases (MMPs) are neutral zinc-dependent endopeptidases with substrate specificity for most extracellular matrix molecules, including collagens, gelatins, fibronectin, laminin and proteoglycan. They depend upon zinc for their catalytic activity.

Most cells do not express MMPs in vivo. Instead, growth factors, hormones, inflammatory cytokines, cell-matrix interactions and cellular transformation regulate their expression. Although the secretory granules of neutrophils and eosinophils are known to store some MMPs, most cell types normally synthesize very low quantities of MMPs.

MMPs share some common structural characteristics that include a signal sequence, an amino-terminal pro-peptide domain, a catalytic zinc binding domain, a proline-rich hinge region, and a carboxy-terminal hemopexin-like domain.

Extracellular matrix degradation is a normal event in the physiological remodeling associated with morphogenesis, reproduction, and in growth and maintenance processes such as cell migration, angiogenesis, and tissue regeneration. During inflammation and in several disease situations excess MMPs may degrade the surrounding proteinaceous matrix, which may result in the destruction or weakening of connective tissue, unregulated cell migration/invasion, and/or tissue fibrosis. For example, connective tissue weakening or destruction may result in diseases such as rheumatoid arthritis, osteoarthritis, chronic periodontis, and arterial and cardiac aneurysm. Accordingly, MMP inhibitors have been used to treat osteoporosis, osteoarthritis, human chronic periodontal disease and various types of aneurysms.

Antimicrobial agents have been used within and/or on medical devices such as intraocular lenses, contact lenses, sutures, meshes, packages containing such devices, and the like. However, some medical devices may not provide effective levels of antimicrobial activity for a sufficient period of time. Moreover, antimicrobial agents on medical devices can be undesirably transferred to their packages, requiring the use of higher levels of antimicrobial agents in order to obtain the desired antimicrobial effect upon implantation or use of the medical devices in vivo.

Accordingly, there is a need for medical devices, packaging materials and textiles that can retain enhanced antimicrobial efficacy. There is also a need for medical devices and compositions that can reduce inflammation and prevent the degradation of the extracellular matrix by MMPs, particularly in response to a disease or injury.

SUMMARY

The present disclosure provides compositions including copolymers possessing furanones in combination with hydroxamates, articles made from or coated with such copolymers or compositions, and methods for making such compositions and articles.

In embodiments, a composition of the present disclosure may include a first component including at least one vinyl phospholipid, a second component of formula:

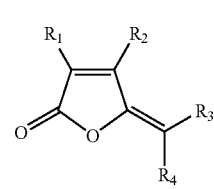

(II)

wherein $R_2$, $R_3$ and $R_4$ are independently or all H or halogen, and $R_1$ is a moiety such as H, halogen, formyl, carboxyl, cyano, ester, amide, alkyl, alkoxy, oxoalkyl, alkenyl, alkynyl, aryl or arylalkyl, wherein at least one of $R_1$, $R_2$, $R_3$ and $R_4$ are substituted with a moiety such as vinyl moieties and acrylate moieties, and a third component including a hydroxamate of the formula:

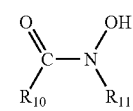

(VIII)

wherein $R_{10}$ may be vinyl groups, hydroxy alkyl acrylate groups, hydroxy alkyl methacrylate groups, alkyl amines, acrylamides, methacrylamides, alkyl groups, alkoxy groups, alkenyl groups, polymers terminated with the foregoing groups, and combinations thereof, and $R_{11}$ may be hydrogen.

In other embodiments, a composition of the present disclosure may include a first component including a phosphorylcholine possessing at least one vinyl group of the formula:

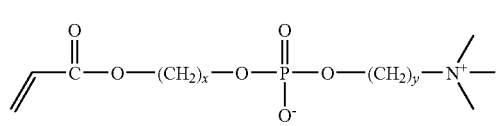

(I)

wherein x is from about 1 to about 10 and y is from about 1 to about 10; a furanone of formula:

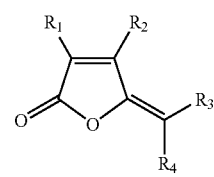

(II)

wherein $R_2$, $R_3$ and $R_4$ are independently or all H or halogen, and $R_1$ is a moiety such as H, halogen, formyl, carboxyl, cyano, ester, amide, alkyl, alkoxy, oxoalkyl, alkenyl, alkynyl, aryl or arylalkyl, wherein at least one of $R_1$, $R_2$, $R_3$ and $R_4$ are substituted with a moiety such as vinyl moieties and acrylate moieties; and a hydroxamate of the formula:

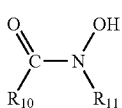

(VIII)

wherein $R_{10}$ may be vinyl groups, hydroxy alkyl acrylate groups, hydroxy alkyl methacrylate groups, alkyl amines, acrylamides, methacrylamides, alkyl groups, alkoxy groups, alkenyl groups, polymers terminated with the foregoing groups, and combinations thereof, and $R_{11}$ may be hydrogen.

In embodiments, an article of the present disclosure may include a first component including at least one vinyl phospholipid; a second component of formula:

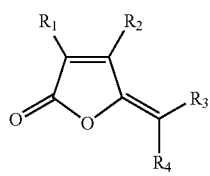

(II)

wherein $R_2$, $R_3$ and $R_4$ are independently or all H or halogen; and $R_1$ is a moiety such as H, halogen, formyl, carboxyl, cyano, ester, amide, alkyl, alkoxy, oxoalkyl, alkenyl, alkynyl, aryl or arylalkyl, wherein at least one of $R_1$, $R_2$, $R_3$ and $R_4$ are substituted with a moiety such as vinyl moieties and acrylate moieties; and a third component including a hydroxamate of the formula:

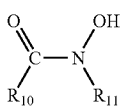

(VIII)

wherein $R_{10}$ may be vinyl groups, hydroxy alkyl acrylate groups, hydroxy alkyl methacrylate groups, alkyl amines, acrylamides, methacrylamides, alkyl groups, alkoxy groups, alkenyl groups, polymers terminated with the foregoing groups, and combinations thereof, and $R_{11}$ may be hydrogen.

In yet other embodiments, a composition of the present disclosure may include a first component including at least one vinyl phospholipid; and a second component including a hydroxamate of the formula:

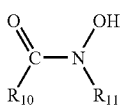

(VIII)

wherein $R_{10}$ may be vinyl groups, hydroxy alkyl acrylate groups, hydroxy alkyl methacrylate groups, alkyl amines, acrylamides, methacrylamides, alkyl groups, alkoxy groups, alkenyl groups, polymers terminated with the foregoing groups, and combinations thereof, and $R_{11}$ may be hydrogen.

DETAILED DESCRIPTION

The present disclosure provides copolymers including at least one vinyl phospholipid monomer, and at least one fura- none. The copolymers may further include at least one hydroxamate as a comonomer, or the furanone/vinyl phospholipid copolymer may be blended with at least one hydroxamate. In other embodiments, compositions of the present disclosure may include at least one vinyl phospholipid and at least one hydroxamate, either as a copolymer, a blend, or both. Compositions including such copolymers and blends are also provided.

The present copolymers may be bioabsorbable or nonabsorbable. As used herein the term "copolymer" includes, but is not limited to, random, block, graft and/or segmented copolymers.

Copolymers of the present disclosure may possess, as a first monomer, at least one phospholipid possessing at least one vinyl group. Such phospholipids are within the purview of those skilled in the art and include, for example, vinyl functional phosphorylcholine monomers, such as 2-methacryloyloxyethyl phosphorylcholine (MPC), 2-acryloyloxyethyl phosphorylcholine, and the like, and combinations thereof. Other phosphorylcholines may be utilized, including phosphorylcholines based upon, or derived from, monomers including, but not limited to, 2-(meth)acryloyloxyethyl-2'-(trimethylammonio)ethyl phosphate; 3-(meth)acryloyloxypropyl-2'-(trimethylammonio)ethyl phosphate; 4-(meth)acryloyloxybutyl-2'-(trimethylammonio)ethyl phosphate; 5-(meth)acryloyloxypentyl-2'-(trimethylammonio)ethyl phosphate; 6-(meth)acryloyloxyhexyl-2'-(trimethylammonio)ethyl phosphate; 2-(meth)acryloyloxyethyl-2'-(triethylammonio)ethyl phosphate; 2-(meth)acryloyloxyethyl-2'-(tripropylammonio)ethyl phosphate; 2-(meth)acryloyloxyethyl-2'-(tributylammonio)ethyl phosphate; 2-(meth)acryloyloxypropyl-2'-(trimethylammonio)ethyl phosphate; 2-(meth)acryloyloxybutyl-2'-(trimethylammonio)ethyl phosphate; 2-(meth)acryloyloxypentyl-2'-(trimethylammonio)ethyl phosphate; 2-(meth)acryloyloxyhexyl-2'-(trimethylammonio)ethyl phosphate; 2-(meth)acryloyloxyethyl-3'-(trimethylammonio)propyl phosphate; 3-(meth)acryloyloxypropyl-3'-(trimethylammonio)propyl phosphate; 4-(meth)acryloyloxybutyl-3'-(trimethylammonio)propyl phosphate; 5-(meth)acryloyloxypentyl-3'-(trimethylammonio)propyl phosphate; 6-(meth)acryloyloxyhexyl-3'-(trimethylammonio)propyl phosphate; 2-(meth)acryloyloxyethyl-4'-(trimethylammonio)butyl phosphate; 3-(meth)acryloyloxypropyl-4'-(trimethylammonio)butyl phosphate; 4-(meth)acryloyloxybutyl-4'-(trimethylammonio)butyl phosphate; 5-(meth)acryloyloxypentyl-4'-(trimethylammonio)butyl phosphate; 6-(meth)acryloyloxyhexyl-4'-(trimethylammonio)butylphosphate; and combinations thereof. As used herein, "(meth)acryl" includes both methacryl and/or acryl groups. Methods for forming phosphorylcholines from such monomers are within the purview of those skilled in the art.

In embodiments, suitable vinyl phosphorylcholines may be of the following formula:

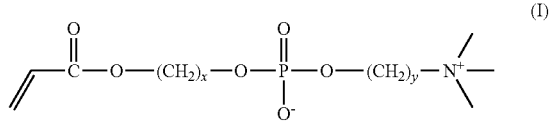

(I)

wherein x is from about 1 to about 10, in embodiments from about 2 to about 6, and y is from about 1 to about 10, in embodiments from about 2 to about 6.

In embodiments, suitable phosphorylcholines include those commercially available as PC 1059, PC 1036, PC 1062, PC 2028, PC 1071, PC 1015, and/or PC 2083 from Biocompatibles Limited (Middlesex, UK).

The copolymers of the present disclosure may be formed by polymerizing the above phospholipid possessing at least one vinyl group with a furanone possessing vinyl and/or acrylate groups. Suitable furanones possessing vinyl and/or acrylate groups for use in forming the copolymers in accordance with the present disclosure include, for example, compounds of formula:

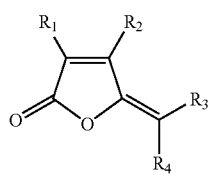

(II)

wherein $R_2$, $R_3$ and $R_4$ are independently or all H or halogen; and $R_1$ is a moiety such as H, halogen, acrylate, formyl, carboxyl, cyano, ester, amide, alkyl, alkoxy, oxoalkyl, alkenyl, alkynyl, aryl or arylalkyl, which moiety may optionally be substituted with one or more substituents; and/or interrupted by one or more hetero atoms; and/or straight chain, branched chain, hydrophobic, hydrophilic, and/or fluorophilic; with the proviso that at least one of $R_1$, $R_2$, $R_3$ and $R_4$ are substituted with a vinyl moiety and/or an acrylate moiety. In embodiments, the furanone possessing vinyl and/or acrylate groups may also be halogenated.

As used herein, "halogen" and/or "halogenated" includes fluorine, chlorine, bromine or iodine.

As used herein, a substituted furanone or substituted moiety includes one possessing a group such as alkyl, cycloalkyl, alkenyl, alkynyl, halo, haloalkyl, haloalkynyl, hydroxy, alkoxy, alkenyloxy, haloalkoxy, haloalkenyloxy, nitro, amino, nitroalkyl, nitroalkenyl, nitroalkynyl, nitroheterocyclyl, alkylamino, dialkylamino, alkenyl amine, alkynylamino, acyl, alkenylacyl, alkynylacyl, acylamino, diacylamino, acyloxy, alkylsulfonyloxy, heterocyclyl, heterocycloxy, heterocyclamino, haloheterocyclyl, alkylsulfenyl, carboalkoxy, alkylthio, acylthio, phosphorus-containing groups such as phosphono and phosphinyl, and combinations thereof.

As used herein, "alkyl", used either alone or in compound words such as "haloalkyl" or "alkylthio", includes straight chain or branched $C_{1-12}$ alkyl groups. Examples include methyl, ethyl, propyl, isopropyl and the like.

As used herein, "alkoxy" includes straight chain or branched alkoxy, in embodiments $C_{1-12}$ alkoxy such as methoxy, ethoxy, n-propoxy, isopropoxy and butoxy isomers.

As used herein, "alkenyl" includes groups formed from straight chain, branched or mono- or polycyclic alkenes including ethylenically mono- or poly-unsaturated alkyl or cycloalkyl groups as previously defined, in embodiments $C_{2-12}$ alkenyl. Examples of alkenyl include vinyl; allyl; 1-methylvinyl; butenyl; iso-butenyl; 3-methyl-2-butenyl; 1-pentenyl; cyclopentenyl; 1-methyl-cyclopentenyl; 1-hexenyl; 3-hexenyl; cyclohexenyl; 1-heptenyl; 3-heptenyl; 1-octenyl; cyclooctenyl; 1-nonenyl; 2-nonenyl; 3-nonenyl; 1-decenyl; 3-decenyl; 1,3-butadienyl; 1-4,pentadienyl; 1,3-cyclopentadienyl; 1,3-hexadienyl; 1,4-hexadienyl; 1,3-cyclohexadienyl; 1,4-cyclohexadienyl; 1,3-cycloheptadienyl; 1,3,5-cycloheptatrienyl; and/or 1,3,5,7-cyclooctatetraenyl.

As used herein, "heteroatoms" include O, N and/or S.

As used herein, "acyl" used either alone or in compound words such as "acyloxy", "acylthio", "acylamino" or "diacylamino" includes carbamoyl, aliphatic acyl groups and acyl groups containing a heterocyclic ring which may be referred to as heterocyclic acyl, in embodiments $C_{1-10}$ acyl. Examples of acyl include carbamoyl; straight chain or branched alkanoyl, such as formyl, acetyl, propanoyl, butanoyl, 2-methylpropanoyl, pentanoyl, 2,2-dimethylpropanoyl, hexanoyl, heptanoyl, octanoyl, nonanoyl, decanoyl; alkoxycarbonyl, such as methoxycarbonyl, ethoxycarbonyl, t-butoxycarbonyl, t-pentyloxycarbonyl or heptyloxycarbonyl; cycloalkylcarbonyl such as cyclopopylcarbonyl cyclobutylcarbonyl, cyclopentylcarbonyl or cyclohexylcarbonyl; alkylsulfonyl, such as methylsulfonyl or ethylsulfonyl; alkoxysulfonyl, such as methoxysulfonyl or ethoxysulfonyl; heterocyclylcarbonyl; heterocyclylalkanoyl, such as pyrrolidinylacetyl, pyrrolidinylpropanoyl, pyrrolidinylbutanoyl, pyrrolidinylpentanoyl, pyrrolidinylhexanoyl or thiazolidinylacetyl; heterocyclylalkenoyl, such as heterocyclylpropenoyl, heterocyclylbutenoyl, heterocyclylpentenoyl or heterocyclylhexenoyl; and/or heterocyclylglyoxyloyl, such as thiazolidinylglyoxyloyl or pyrrolidinylglyoxyloyl.

As used herein, "fluorophilic" includes the highly attractive interactions certain groups, such as highly fluorinated alkyl groups of $C_4$-$C_{10}$ chain length, have for perfluoroalkanes and perfluoroalkane polymers.

In other embodiments, a suitable furanone may be of the following formula:

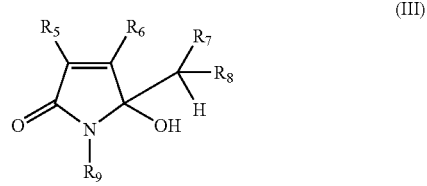

(III)

wherein $R_5$ and $R_6$ are independently H, halogen, hydroxy, substituted or unsubstituted alkyl, substituted or unsubstituted alkoxy, substituted or unsubstituted oxoalkyl, substituted or unsubstituted alkenyl, substituted or unsubstituted aryl, or substituted or unsubstituted arylalkyl, optionally interrupted by one or more hetero atoms, straight chain or branched chain, hydrophilic or fluorophilic, $R_7$ and $R_8$ are independently H, halogen, substituted or unsubstituted alkyl, substituted or unsubstituted alkoxy, substituted or unsubstituted aryl, or substituted or unsubstituted arylalkyl, and $R_9$ is H, hydroxy, substituted or unsubstituted alkyl, substituted or unsubstituted alkoxy, substituted or unsubstituted oxoalkyl, substituted or unsubstituted alkenyl, substituted or unsubstituted aryl or substituted or unsubstituted arylalkyl, optionally interrupted by one or more hetero atoms, straight chain or branched chain, hydrophilic or fluorophilic.

Specific examples of such compounds of formula III include, for example, the following:

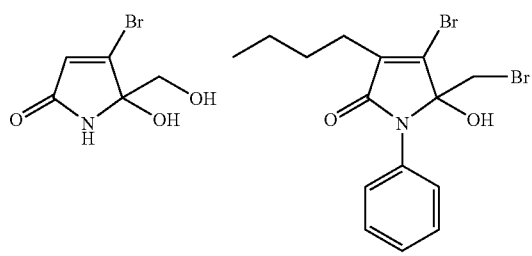
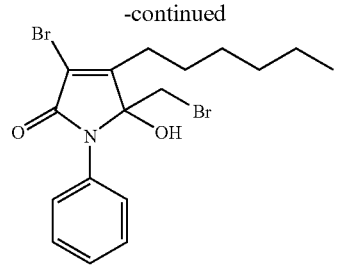
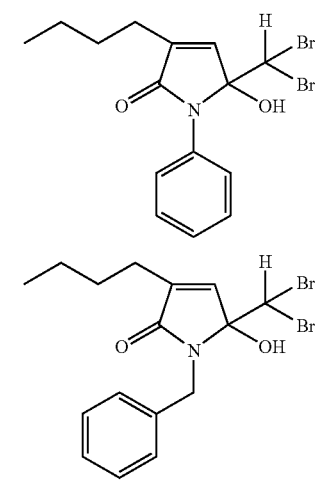
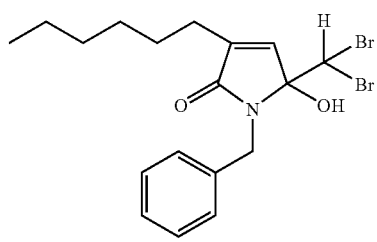
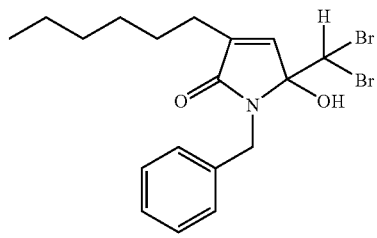
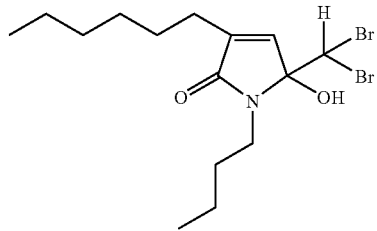
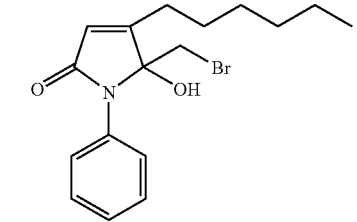
In some embodiments, the above furanones of formula III may be dehydrated to form another suitable furanone compound of the following formula IV:
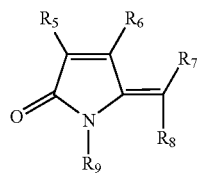
(IV)
wherein $R_5$, $R_6$, $R_7$, $R_8$, and $R_9$ are as defined above.
Specific examples of compounds of formula IV include the following:
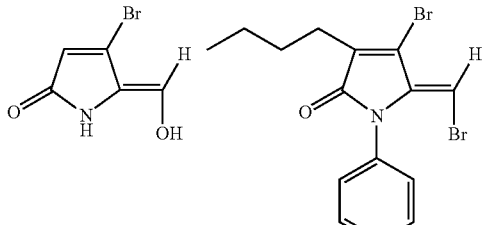
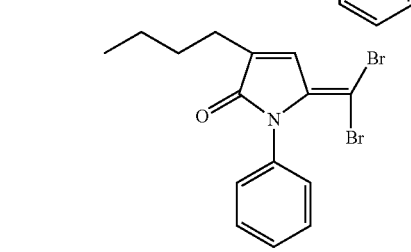
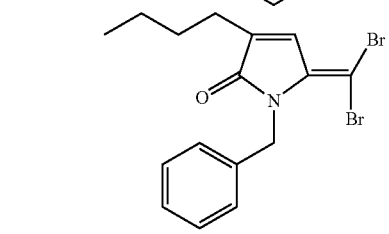
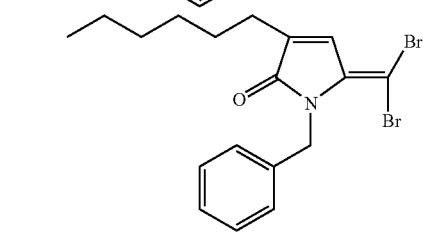
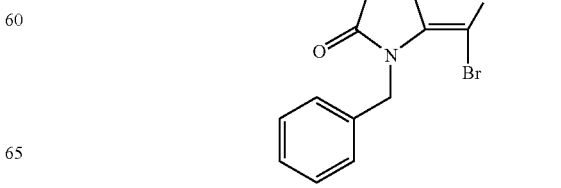

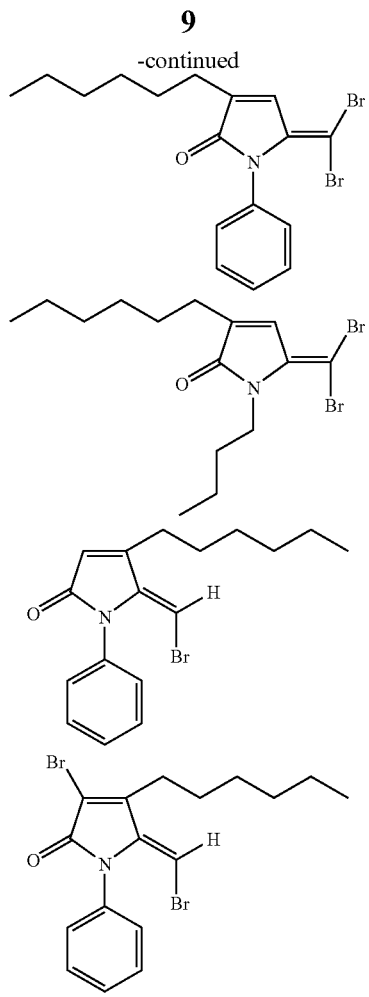

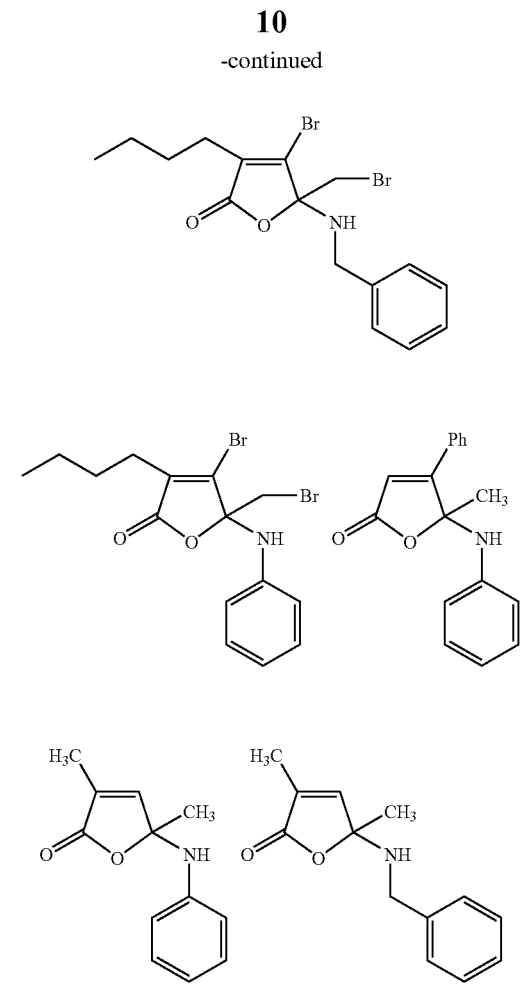

Other suitable furanone derivatives may include, in embodiments, those of the following formula:

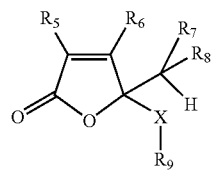

(V)

wherein $R_5$, $R_6$, $R_7$, $R_8$ and $R_9$ are as defined above and X is O or $NR_5$.

Specific examples of furanones of formula V include, but are not limited to, the following:

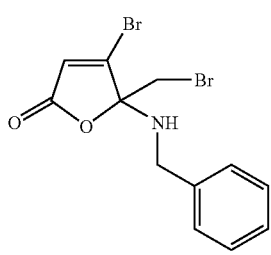

Yet other suitable furanones include those of the following formula:

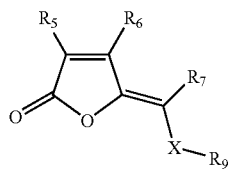

(VI)

wherein $R_5$, $R_6$, $R_7$ and $R_9$ are as defined above, and X is O or $NR_5$.

Specific examples of furanones of formula VI include, but are not limited to, the following:

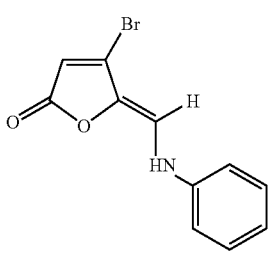

-continued

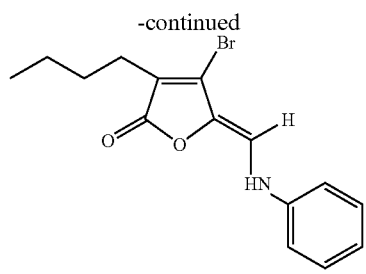

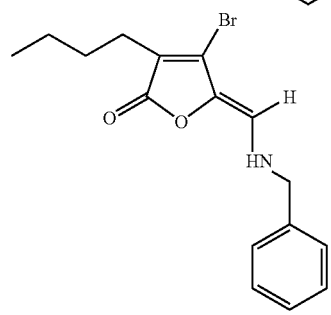

Yet other suitable furanones include those of the following formula:

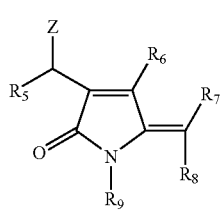 (VII)

wherein $R_5$, $R_6$, $R_7$, $R_8$ and $R_9$ are as defined above, and Z is $R_6$, halogen, $OC(O)R_6$, $=O$, amine, azide, thiol, mercaptoaryl, arylalkoxy, mercaptoarylalkyl, $SC(O)R_6$, $OS(O)_2R_6$, $NHC(O)R_6$, $=NR_6$, or $NHR_6$.

Specific examples of compounds of formula VII include, but are not limited to, the following:

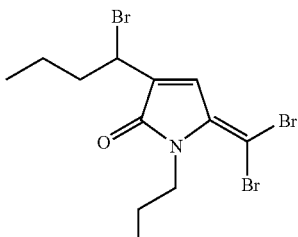

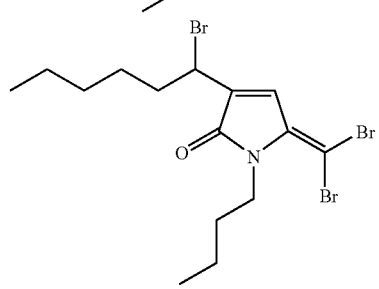

-continued

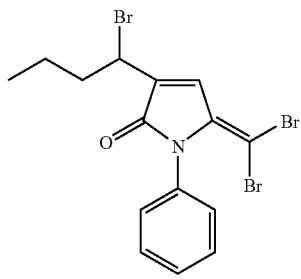

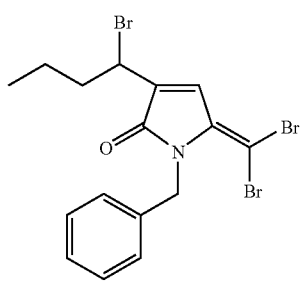

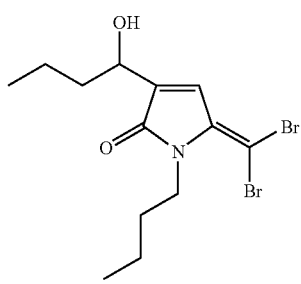

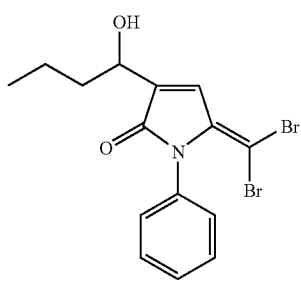

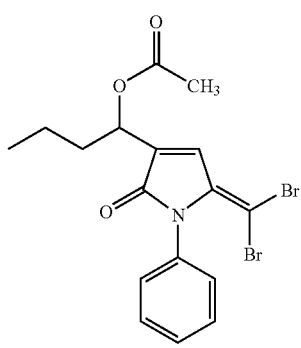

-continued

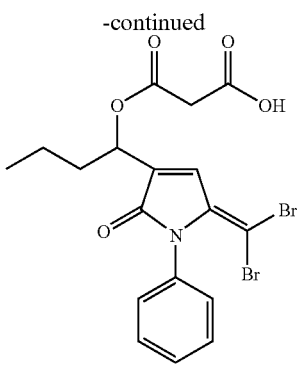

Furanones, including halogenated furanones and/or hydroxyl furanones, are known as inhibitors of quorum sensing. Quorum sensing, also known as bacterial signaling, is recognized as a general mechanism for gene regulation in many bacteria, and it allows bacteria to perform in unison such activities as bioluminescence, swarming, biofilm formation, production of proteolytic enzymes, synthesis of antibiotics, development of genetic competence, plasmid conjugal transfer, and spoliation. Quorum sensing is a universal regulatory mechanism used by both Gram-positive bacteria such as *Staphylococcus aureus, Streptococcus pneumoniae, Salmonella enteritidis, Staphylococcus epideimidis, Bacillus subtilis*, and the like, and Gram-negative bacteria such as *Pseudomonas aeruginosa, Escherichia coli, Aeromonas hydrophila*, and the like.

Furanones, including halogenated and/or hydroxyl furanones, may also block quorum sensing and inhibit the growth of bacteria in amounts that are non-toxic to mammalian cells. Given their mechanism of action, furanones' antipathogenic properties may be effective against a broad spectrum of infectious agents and may be able to reduce and/or prevent colonization of both gram positive and gram negative bacteria, including those noted above.

In accordance with the present disclosure, a quorum sensing inhibitor, such as the furanones described above, optionally possessing a vinyl and/or acrylate group described herein, in embodiments also possessing halogen and/or hydroxyl groups, may act as an antimicrobial agent by inhibiting microbial development and proliferation. As noted above, the furanone, acting as a quorum sensing inhibitor, may inhibit swarming motility and biofilm formation, both of which frequently underlie the pathophysiology of infectious diseases. The inhibition of swarming and biofilm formation may thus reduce bacterial burden and hence prevent infection and disease progression.

In addition, unlike antibiotics and antiseptic compounds which kill microbes and carry the risk of inducing antimicrobial resistance, furanones, including halogenated and/or hydroxyl furanones described herein do not exert such evolutionary pressures. Thus, antimicrobial resistance to an article made with or coated with a copolymer of the present disclosure is not a concern.

Conditions for conducting the copolymerization of the above furanones with the at least one phospholipid possessing at least one vinyl group are within the purview of those skilled in the art. The copolymerization can be achieved by reacting the at least one phospholipid possessing at least one vinyl group with a furanone possessing a vinyl and/or acrylate group. The conditions under which the at least one phospholipid possessing at least one vinyl group may be reacted with the furanone may vary widely depending on the specific phospholipid, the specific furanone being employed, and the desired degree of polymerization to be achieved. The molar ratio of phospholipid to furanone may be from about 1:10 to about 10:1. In embodiments, the amount of furanone employed can be from about 2 to about 8 moles of furanone per mole of phospholipid possessing at least one vinyl group. Suitable reaction times and temperatures can be from about 15 minutes to about 72 hours, in embodiments from about 60 minutes to about 24 hours, at temperatures of from about 0° C. to about 250° C., in embodiments from about 25° C. to about 80° C.

In embodiments, the copolymers of the present disclosure may be prepared from monomer solutions prepared by dissolving the furanone possessing vinyl or acrylate groups in a liquid vinyl monomer or monomer solution, for example the at least one phospholipid possessing at least one vinyl group. Suitable solvents which may be utilized in forming such solutions include, for example, water, lower alcohols, mixtures of the foregoing, and the like. In other embodiments, an aqueous solution or suspension may be formed with the furanone possessing vinyl and/or acrylate groups in combination with the at least one phospholipid possessing at least one vinyl group. In yet other embodiments, the furanone possessing vinyl or acrylate groups may be combined with an organic solvent and the resulting solution may then be mixed or emulsified with an aqueous compatible or incompatible solution containing the at least one phospholipid possessing at least one vinyl group. Suitable organic solvents include, for example, ethanol, methanol, isopropanol, chloroform, methylene chloride, combinations thereof, and the like.

In embodiments, the copolymers of the above furanones and the at least one phospholipid possessing at least one vinyl group may be copolymerized with hydroxamates to form a copolymer of the present disclosure. In other embodiments, the copolymers of the above furanones and the at least one phospholipid possessing at least one vinyl group may be blended with hydroxamates to form a composition of the present disclosure. In yet other embodiments, a composition of the present disclosure may include at least one phospholipid possessing at least one vinyl group in combination with at least one hydroxamate, either as a copolymer or blend.

Suitable hydroxamates for combination with the above components, either as comonomers or as a blend, include components possessing a hydroxamate group of the following formula (VIII):

(VIII)

wherein $R_{10}$ may include vinyl groups, including vinyl alcohols such as polyvinyl alcohol, hydroxy acrylate groups including hydroxy alkyl acrylates, hydroxy methacrylate groups including hydroxy alkyl methacrylates, hydroxyethyl methacrylates, acid groups including acrylic acid, methacrylic acid, alkyl amines, acrylamides, methacrylamides, other alkyl groups, alkoxy groups, alkenyl groups, and polymers possessing hydroxyl groups, including polymers terminated with any of the above groups, such as vinyl alcohols, hydroxyethyl methacrylates, and the like, and $R_{11}$ may be hydrogen.

As used herein, "alkyl", used either alone or in compound words such as "haloalkyl" or "alkylthio", includes straight chain or branched $C_{1-12}$ alkyl groups. Examples include methyl, ethyl, propyl, isopropyl and the like.

As used herein, "alkoxy" includes straight chain or branched alkoxy, in embodiments $C_{1-12}$ alkoxy such as methoxy, ethoxy, n-propoxy, isopropoxy and butoxy isomers.

As used herein, "alkenyl" includes groups formed from straight chain, branched or mono- or polycyclic alkenes including ethylenically mono- or poly-unsaturated alkyl or cycloalkyl groups as previously defined, in embodiments $C_{2-12}$ alkenyl. Examples of alkenyl include vinyl; allyl; 1-methylvinyl; butenyl; iso-butenyl; 3-methyl-2-butenyl; 1-pentenyl; cyclopentenyl; 1-methyl-cyclopentenyl; 1-hexenyl; 3-hexenyl; cyclohexenyl; 1-heptenyl; 3-heptenyl; 1-octenyl; cyclooctenyl; 1-nonenyl; 2-nonenyl; 3-nonenyl; 1-decenyl; 3-decenyl; 1,3-butadienyl; 1-4,pentadienyl; 1,3-cyclopentadienyl; 1,3-hexadienyl; 1,4-hexadienyl; 1,3-cyclohexadienyl; 1,4-cyclohexadienyl; 1,3-cycloheptadienyl; 1,3,5-cycloheptatrienyl; or 1,3,5,7-cyclooctatetraenyl.

Methods for forming these hydroxamate functional compositions are within the purview of those skilled in the art. For example, in embodiments, a hydroxamate functional polymer may be produced by the surface modification of cross-linked polymethacrylic acid (PMAA)-co-methyl methacrylate (MAA) beads, thus producing a hydroxamate functional polymer, i.e., PMAA-MMA-hydroxamate as the hydroxamate functional composition.

In other embodiments, polymerizable hydroxamate monomers may be synthesized which may be copolymerized with the furanones and the at least one phospholipid possessing at least one vinyl group, or blended therewith. The hydroxamate monomer, which may be encompassed by formula VIII above, may have an $R_{10}$ including $CH_2=C-CH_3$, and $R_{11}$ may be hydrogen. In other embodiments, the hydroxamate monomer may be utilized to synthesize a hydroxamate homopolymer, or may be copolymerized with any other suitable comonomers to produce copolymers which, in turn, may be copolymerized with the furanones and the at least one phospholipid possessing at least one vinyl group, or blended therewith.

Hydroxamate homopolymers synthesized from the above hydroxamate monomer can also be grafted onto any derivatizable polymer. The resulting hydroxamate functional composition, whether a monomer, homopolymer, or copolymer, may then be combined with the copolymer including the above furanones and the at least one phospholipid possessing at least one vinyl group, either as a comonomer or as a blend.

It should, of course, be understood that two or more hydroxamates may be utilized in forming a copolymer or blend.

In other embodiments, as noted above, the hydroxamates may be copolymerized or blended with the phospholipids possessing at least one vinyl group, without a furanone. For example, monomers such as MPC and n-hydroxy methacrylamide (NHMAA) may be polymerized by conventional free radical, living radical, Atom Transfer Radical (ATR), or radiation polymerization techniques. Such techniques are within the purview of those skilled in the art. The solubility, amphiphilicity, and swellability of the resulting composition, in embodiments a copolymer, may be controlled by incorporating other monomers into the composition. Such additional monomers include, for example, acrylate or methacrylate monomers such as methyl methacrylate, butyl methacrylate, hexyl methacrylate, octyl methacrylate, combinations thereof, and the like.

Additional wound healing properties may be imparted to the copolymer or blend by incorporating additional monomers having a cationic charge into the copolymer or blend. Such monomers having a cationic charge include, but are not limited to, 2-(diethylamino)ethyl methacrylate; 2-(dimethylamino)ethyl methacrylate; acrylates including 2-(diethylamino)ethyl acrylate, 2-(dimethylamino)ethyl acrylate, combinations thereof, and the like.

Additional functionality, including angiogenic properties, anti-inflammatory properties, enzymatic inhibition properties, and the like, may be imparted by the addition of anionic monomers. Suitable anionic monomers include, for example, acrylic acid, methacrylic acid, itaconic acid, maleic acid, fumaric acid, vinyl sulfonic acid, sulfopropyl acrylate, combinations thereof, and the like. These monomers may be blended or copolymerized with the phospholipid, the hydroxamate, or both.

Similarly, antimicrobial properties may be provided to the compositions by the addition of monomers containing quaternary ammonium groups such as 2-(methacryloxyethyl) trimethyl ammonium chloride.

Conditions for conducting polymerization of the hydroxamates with the furanones and/or phospholipids, in embodiments furanone/phospholipid copolymers, are within the purview of those skilled in the art and include those described above for the polymerization of the furanones and the at least one phospholipid possessing at least one vinyl group.

Polymerization may also be initiated by subjecting the monomers, for example, the at least one phospholipid possessing at least one vinyl group, and/or furanone possessing vinyl and/or acrylate groups, and/or hydroxamate, to energy including irradiation, such as high energy radiation including gamma and/or e-beam, ultraviolet (UV) light, pulse laser ablation deposition, plasma energy treatment, chemical initiation, photoinitiation, and the like. In embodiments, the use of high energy radiation initiation may be beneficial as it should not require the use of an additional initiator such as a chemical initiator or catalyst.

In embodiments, a copolymer of the present disclosure may possess the vinyl phospholipid in amounts of from about 5 to about 95 percent by weight of the copolymer, in embodiments from about 15 to about 85 percent by weight of the copolymer. Thus, the copolymer of the present disclosure may possess the furanone possessing vinyl and/or acrylate groups, or the hydroxamate, in amounts of from about 5 to about 95 percent by weight of the copolymer, in embodiments from about 15 to about 85 percent by weight of the copolymer.

A composition including the above furanone/phospholipid copolymer with the hydroxamate as a blend, would include the furanone/vinyl phospholipid copolymer in an amount of from about 1 percent by weight of the composition to about 99 percent by weight of the composition, in embodiments from about 5 percent by weight of the composition to about 95 percent by weight of the composition, with the hydroxamate present in an amount of from about 1 percent by weight of the composition to about 99 percent by weight of the composition, in embodiments from about 5 percent by weight of the composition to about 95 percent by weight of the composition.

Where the hydroxamate is included as a comonomer with the furanone/vinyl phospholipid copolymer, the resulting copolymer may possess the furanone in an amount of from about 1 percent by weight of the copolymer to about 98 percent by weight of the copolymer, in embodiments from about 5 percent by weight of the copolymer to about 90 percent by weight of the copolymer; the vinyl phospholipid may be present in an amount of from about 1 percent by weight of the copolymer to about 98 percent by weight of the copolymer, in embodiments from about 5 percent by weight of the copolymer to about 90 percent by weight of the copolymer; and the hydroxamate may be present in an amount of from about 1 percent by weight of the copolymer to about 98 percent by weight of the copolymer, in embodiments from about 5 percent by weight of the copolymer to about 90 percent by weight of the copolymer.

In other embodiments, the above hydroxamates may be copolymerized or blended with a furanone, without the phospholipid. In other embodiments, the above hydroxamates may be copolymerized or blended with a phospholipid, without the furanone. Suitable conditions for conducting the polymerization of a hydroxamate with a furanone, and/or the polymerization of a hydroxamate with a phospholipid, include those described herein for polymerization of a hydroxamate with a furanone/phospholipid copolymer, as well as those described above for the polymerization of the furanone and the at least one phospholipid possessing at least one vinyl group.

Where the composition of the present disclosure includes a phospholipid and hydroxamate as a copolymer or blend, the phospholipid may be present in an amount of from about 5% to about 95% by weight of the composition, in embodiments from about 15% to about 85% by weight of the composition, with the hydroxamate present in an amount of from about 5% to about 95% by weight of the composition, in embodiments from about 15% to about 85% by weight of the composition.

In embodiments, the phospholipid possessing at least one vinyl group, the furanone possessing vinyl and/or acrylate groups, and optional halogen and/or hydroxyl groups, and optionally the hydroxamate, may also be copolymerized in the presence of additional vinyl or acrylate monomers, optionally possessing the hydroxamate groups described above, to obtain copolymers possessing excellent solubility, wettability, thermal properties, film-forming properties, and the like. Such additional vinyl or acrylate monomers may include, for example, vinyl functional quaternary amines, hydroxyethyl methacrylate, n-vinyl pyrrolidone, sodium acrylate, bis-acrylate, styrene sulfonic acid, butyl acrylate, sulfopropyl acrylate, sulfopropyl methacylate, acrylamide, diacrylamide, methacrylic acid, acrylic acid, polyethylene glycol acrylates, polyethylene glycol/polypropylene glycol acrylates, silicone acrylates, combinations thereof, and the like. In addition to forming copolymers with the phospholipid possessing at least one vinyl group and the furanone possessing vinyl and/or acrylate groups, in some embodiments these additional vinyl or acrylate monomers may be combined with the copolymers of the present disclosure as a mixture or blend.

For example, in some embodiments a copolymer of the present disclosure may include a random copolymer of the phospholipid possessing at least one vinyl group, the furanone possessing vinyl and/or acrylate groups, and the additional vinyl or acrylate monomer including the hydroxamate functional group.

In embodiments, the furanone possessing vinyl or acrylate groups and the at least one phospholipid possessing at least one vinyl group may be placed into a solution with an additional acrylate or vinyl compound possessing a hydroxamate group. For example, in some embodiments, a furanone acrylate and MPC may be placed into solution with the PMAA-MMA-hydroxamate described above (at a ratio of about 50 to about 25 to about 25) and polymerized by subjecting the monomers to gamma radiation to produce a copolymer. The resulting copolymer may, in embodiments, be in the form of a hydrogel.

The compositions of the present disclosure including hydroxamates may be used in wound treatment, or in the formation of medical devices and implants. Chronic wounds may take months or years to heal due, in part, to high levels of MMPs that degrade the newly formed matrix even as it is synthesized. The compositions of the present disclosure including hydroxamates, due to the presence of the hydroxamate group, may inhibit the activity of the MMPs in or adjacent a wound, thereby promoting healing.

Similarly, angiogenesis or vasculogenesis of tumors and the formation of metastases require cell migration and invasion, which are enabled by the release of pro-MMPs. The compositions of the present disclosure including hydroxamates, which counteract those MMPs, may thus be suitable for minimizing angiogenesis and/or vascularization of tumors.

Furthermore tissue remodeling occurs secondary to secretion or expression of MMP's. Thus blood vessels associated with wound repair are resorbed or ischemic tissue is destroyed by MMP action. The compositions of the present disclosure including hydroxamates, which counteract those MMPs, may thus be suitable to enhance would repair.

The activity of MMPs is also essential for many of the processes involved in atherosclerotic plaque formation (infiltration of inflammatory cells, angiogenesis, and smooth muscle cell migration and proliferation). Elevated levels of MMPs are expressed in human atherosclerotic plaque and at the sites of aneurysm. Furthermore, matrix degradation by MMPs may cause the plaque instability and rupture that leads to the clinical symptoms of atherosclerosis. The compositions of the present disclosure including hydroxamates, which counteract those MMPs, may thus be suitable to reduce the formation of atherosclerotic plaques and the incidence of rupture at the sites of aneurysm.

In the context of arthritis, a similar role for activated MMPs in cartilage degradation has been demonstrated. Elevated concentrations and activities of several MMPs including MMP-1, MMP-3, MMP-8 and MMP-13, as well as aggrecanase (another metalloproteinase) have been identified in the synovial fluid of osteoarthritis and rheumatoid arthritis patients. The compositions of the present disclosure including hydroxamates, which counteract those MMPs, may thus be suitable to treat arthritis and/or minimize the degradation of cartilage.

There is also accumulating evidence that an increase in the proportion of active MMPs is associated with the progression of restenosis following vascular interventions such as balloon angioplasty or intra-coronary stenting, for the treatment of coronary artery disease. In contrast to the non-diseased vessel wall, which constitutively expresses only pro-(inactive) MMP-2, injured or atherosclerotic arteries demonstrate a dramatic increase in MMP-2 activity. This occurs in conjunction with induced expression of MMPs-3, -7, -9, -12, and -13. The compositions of the present disclosure including hydroxamates, which counteract those MMPs, may thus be utilized to reduce restenosis.

The compositions of the present disclosure including hydroxamates may inactivate MMPs by binding the zinc at the active center of the enzymes. With multiple point attachments, the hydroxamates behave like a molecular magnet for zinc.

In embodiments, the compositions of the present disclosure possessing hydroxamates may bind to the active form of MMPs, without and specificity for particular MMP types. In other embodiments, the compositions of the present disclosure possessing hydroxamates may provide preferential binding to active forms of MMPs in the local tissue environment. This may be advantageous because it specifically targets one stage in the MMP regulatory cascade, namely that directly preceding matrix degradation. In addition, selective binding may reduce the risk of over inhibition which would delay healing by preventing a healthy rate of tissue turnover and essential processes such as cell migration and angiogenesis.

The copolymers thus produced may have a furanone and/or a hydroxamate attached via a hydrolytically degradable bonds at the head of the polymer chain. Advantageously, upon hydrolysis, the present copolymers may release low concentrations of the furanone and/or hydroxamate, thus providing antimicrobial properties where a furanone is released, and inhibition of MMP activity, where the hydroxamate is released, at the site of implantation or injury to which the copolymer or an article including the composition of the present disclosure is applied.

The resulting compositions of the present disclosure, including phospholipids, hydroxamates, and/or furanones, may be suitable for coating other materials, made into a solid material after conventional thermoplastic processing (molding, extrusion, etc.), or made into beads or nanoparticles by spray drying, solvent evaporation or any other conventional polymer processing method.

In embodiments, articles prepared from or coated with a composition of the present disclosure possessing a furanone and/or hydroxamate, optionally as a copolymer blend, may thus display improved resistance to bacteria. The resulting compositions may also have MMP-inhibiting properties, which may enhance wound healing.

The compositions of the present disclosure may find many uses in the formation of medical devices and coatings thereon. In embodiments, surgical articles can be manufactured from the compositions described herein. Suitable medical devices include, but are not limited to, clips and other fasteners, staples, tacks, sutures, pins, screws, prosthetic devices, wound dressings, bandages, drug delivery devices, anastomosis rings, surgical blades, contact lenses, intraocular lenses, surgical meshes including hernia meshes, stents, stent coatings, grafts, tissue patches, catheters, stent/grafts, knotless wound closures, sealants, adhesives, contact lenses, intraocular lenses, anti-adhesion devices, anchors, tunnels, bone fillers, synthetic tendons, synthetic ligaments, tissue scaffolds, stapling devices, buttresses, lapbands, orthopedic hardware, pacers, pacemakers, drug delivery devices, soft tissue repair devices (including mesh fixation) and other implants and implantable devices.

Fibers can be made from the compositions of the present disclosure. In embodiments, fibers made of compositions of the present disclosure may be knitted or woven with other fibers, either absorbable or non-absorbable fibers, to form textiles. The fibers also can be made into non-woven materials to form fabrics, such as meshes and felts.

The present copolymers or blends of the present disclosure can be formed into articles using any technique within the purview of those skilled in the art, such as, for example, extrusion, molding and/or solvent casting. The copolymers and/or blends herein can be used alone or combined with other polymers, which may be either absorbable or non-absorbable. Copolymers and/or blends of the present disclosure, optionally combined with other materials, may be referred to, in embodiments, as compositions of the present disclosure. Methods for forming articles with the compositions of the present disclosure are within the purview of those skilled in the art.

Packaging materials which may formed with the compositions of the present disclosure include packaging for products such as medical devices, pharmaceuticals, textiles, consumer goods, foods, and the like.

Copolymers or blends of the present disclosure may also be used to form coatings for articles, including textiles, medical devices, and packaging materials. Coatings may be applied to at least a portion of the surface of an article, including the interior, exterior, or both.

In embodiments, the coating of the present disclosure can be applied as a solution and the solvent evaporated to leave the coating components, in embodiments, the furanose, phospholipid, and hydroxamate of the present disclosure. Suitable solvents which may be utilized in forming the solution include any solvent or combination of solvents suitable for the chosen coating composition. To be suitable, the solvent must (1) be miscible with the coating components, and (2) not appreciably affect the integrity of any material used to form the article being coated, such as a suture. Some examples of suitable solvents include alcohols, ketones, ethers, aldehydes, acetonitrile, acetic acid, methylene chloride, chloroform and water. In embodiments, methylene chloride may be used as a solvent.

Medical devices and packaging materials in accordance with the present disclosure can be sterilized in accordance with techniques within the purview of those skilled in the art.

Preparing a coating solution of the present disclosure may be a relatively simple procedure and can be accomplished by blending, mixing, and the like. In one embodiment, where a composition of the present disclosure and a solvent such as methylene chloride are utilized to form the coating solution, the desired amount of composition may be placed into a container, followed by the addition of the desired amount of methylene chloride. The two ingredients may then be mixed thoroughly to combine the ingredients.

Any technique within the purview of those skilled in the art may be employed for applying the coating solution or suspension to the article. Suitable techniques include dipping, spraying, wiping and brushing. The article wetted with the coating solution or suspension may be subsequently passed through or held in a drying oven for a time and at a temperature sufficient to vaporize and drive off the solvent.

In addition, the present disclosure provides methods for surface/bulk modification of devices by impregnating a device such as a medical device with monomer solutions of the vinyl phospholipid, and/or furanone possessing vinyl and/or acrylate groups, and/or hydroxamates, for example by immersion, and in situ polymerizing the monomer solutions to prepare graft copolymers or an interpenetrating network of the copolymers of the present disclosure in combination with the device.

Solutions may also be used with chemical couplers, for example silanes, vinyl siloxanes, and the like, to not only graft or interpenetrate the surface of a medical device, but to also covalently tether the copolymers of the present disclosure to the surface of a device.

Medical devices possessing a coating of the present disclosure may be formed of copolymers or blends of the present disclosure. In other embodiments, medical devices can also be formed of absorbable materials, nonabsorbable materials, and combinations thereof. Suitable absorbable materials which may be utilized to form the medical device include trimethylene carbonate, caprolactone, dioxanone, glycolic acid, lactic acid, homopolymers thereof, copolymers thereof, and combinations thereof. Suitable non-absorbable materials which may be utilized to form the medical device include polyolefins, such as polyethylene, polypropylene, copolymers of polyethylene and polypropylene, blends of polyethylene and polypropylene, polyesters such as polyethylene terephthalate, polyimides, polyamides, combinations thereof, and the like.

Textiles which may be coated with compositions of the present disclosure include fibers made of copolymers or blends of the present disclosure, as well as other natural fibers, synthetic fibers, blends of natural fibers, blends of synthetic fibers, and blends of natural fibers with synthetic fibers. Suitable other materials utilized to form textiles include polyesters, polyamides, polyolefins, halogenated polymers, polyester/polyethers, polyurethanes, homopolymers thereof, copolymers thereof, and combinations thereof. Specific examples of suitable materials include polyethylene, polypropylene, polybutylene, polyvinyl chloride, polyethylene terephthalate, nylon 6, and nylon 6,6.

In some embodiments, compositions in accordance with the present disclosure may be formed by combining the copolymers or blends of the present disclosure with other additional components. In embodiments, coating compositions of the present disclosure may be combined with a fatty acid component, such as a fatty acid or a fatty acid salt or a salt of a fatty acid ester. Suitable fatty acids may be saturated or unsaturated, and may include higher fatty acids having more than about 12 carbon atoms. Suitable saturated fatty acids include, for example, stearic acid, palmitic acid, myristic acid and lauric acid. Suitable unsaturated fatty acids include oleic acid, linoleic acid, and linolenic acid. In addition, an ester of fatty acids, such as sorbitan tristearate or hydrogenated castor oil, may be used.

Suitable fatty acid salts include the polyvalent metal ion salts of $C_6$ and higher fatty acids, particularly those having from about 12 to about 22 carbon atoms, and mixtures thereof. Fatty acid salts including the calcium, magnesium, barium, aluminum, and zinc salts of stearic, palmitic and oleic acids may be useful in some embodiments of the present disclosure. Some useful salts include commercial "food grade" calcium stearate which contains a mixture of about one-third $C_{16}$ and two-thirds $C_{18}$ fatty acids, with small amounts of the $C_{14}$ and $C_{22}$ fatty acids.

Suitable salts of fatty acid esters which may be included in the compositions of the present disclosure include calcium, magnesium, aluminum, barium, or zinc stearoyl lactylate; calcium, magnesium, aluminum, barium, or zinc palmityl lactylate; and/or calcium, magnesium, aluminum, barium, or zinc oleyl lactylate. In embodiments; calcium stearoyl-2-lactylate (such as the calcium stearoyl-2-lactylate commercially available under the tradename VERV from American Ingredients Co., Kansas City, Mo.) may be utilized. Other fatty acid ester salts which may be utilized include those selected from the group consisting of lithium stearoyl lactylate, potassium stearoyl lactylate, rubidium stearoyl lactylate, cesium stearoyl lactylate, francium stearoyl lactylate, sodium palmityl lactylate, lithium palmityl lactylate, potassium palmityl lactylate, rubidium palmityl lactylate, cesium palmityl lactylate, francium palmityl lactylate, sodium oleyl lactylate, lithium oleyl lactylate, potassium oleyl lactylate, rubidium oleyl lactylate, cesium oleyl lactylate, and francium oleyl lactylate.

Where utilized, the amount of fatty acid component can be from about 5 percent to about 60 percent by weight of the total composition of the present disclosure. In embodiments, the fatty acid component may be present in an amount from about 15 percent to about 55 percent by weight of the total composition.

In one embodiment, the copolymer or blend including the phospholipid, furanone, and hydroxamate, can be present in an amount from about 45 to about 60 weight percent of the composition and the fatty acid component, such as a fatty acid salt or a salt of a fatty acid ester, can be present in an amount from about 40 to about 55 weight percent of the composition. In embodiments, the phospholipid, furanone and hydroxamate can be present in an amount from about 50 to about 55 weight percent of the composition and the fatty acid component can be present in an amount from about 45 to about 50 weight percent of the composition.

In embodiments, a fatty acid component as described above, including a calcium stearoyl lactate, may be combined with a copolymer or blend of the present disclosure or included in any coating solution utilized to apply a copolymer or blend of the present disclosure to a medical article, packaging, textile, and the like.

In other embodiments, the copolymers or blends of the present disclosure may be combined with additional polymeric materials, such as oligomers and/or polymers. The additional polymeric materials can be bioabsorbable or non-absorbable. Bioabsorbable polymers which may be utilized in the composition are within the purview of those skilled in the art and include those containing linkages derived from monomers including, for example, glycolide, lactide, glycolic acid, lactic acid, caprolactone, trimethylene carbonate, dioxanones, dioxepanones, and the like, and homopolymers, copolymers and combinations thereof. Similarly, polyorthoesters, polyhydroxy butyrates, polytyrosine carbonates, polyhydroxy alkanoates, combinations thereof, and the like, may be added. The additional polymeric materials may be blended with or bonded to the copolymers or blends of the present disclosure (e.g., to create a block copolymer).

In embodiments, the copolymers or blends of the present disclosure may be combined with polyalkylene oxides such as polyethylene oxides, polyethylene glycol, polypropylene glycol, copolymers thereof, and the like, including those having acrylate groups such as acrylate PEGs, and/or acrylate PEG/PPG copolymers. Such combinations may include copolymers or blends of the present disclosure with polyalkylene oxide oligomers and/or polymers and/or other non-toxic surfactants. The resulting composition may thus possess antimicrobial and MMP-inhibiting properties due to the presence of the copolymers or blends described above. In other embodiments, the copolymers or blends of the present disclosure may be combined with silicone acrylates.

If desired, in addition to the copolymers or blends of the present disclosure, compositions described herein can optionally contain additional components, e.g., dyes, antimicrobial agents, growth factors, anti-inflammatory agents, and the like. The term "antimicrobial agent" as used in the present disclosure includes antibiotics, antiseptics, disinfectants and combinations thereof. In embodiments, the antimicrobial agent may be an antiseptic, such as triclosan or one of the furanones described above.

Classes of antibiotics that can be combined with the compositions of the present disclosure include tetracyclines like minocycline; rifamycins like rifampin; macrolides like erythromycin; penicillins like nafcillin; cephalosporins like cefazolin; beta-lactam antibiotics like imipenem and aztreonam; aminoglycosides like gentamicin and TOBRAMYCIN®; chloramphenicol; sulfonamides like sulfamethoxazole; glycopeptides like vancomycin; quinolones like ciprofloxacin; fusidic acid; trimethoprim; metronidazole; clindamycin; mupirocin; polyenes like amphotericin B; azoles like fluconazole; and beta-lactam inhibitors like sulbactam. Other antimicrobials which may be added include, for example, antimicrobial peptides and/or proteins, chemotherapeutic drugs, telomerase inhibitors, other furanones including 5-furanones, mitoxanthone, and the like.

Examples of antiseptics and disinfectants which may be combined with the compositions of the present disclosure include hexachlorophene; cationic biguanides like chlorhexidine and cyclohexidine; iodine and iodophores like povidone-iodine; halo-substituted phenolic compounds like PCMX (i.e., p-chloro-m-xylenol) and triclosan (i.e., 2,4,4'-trichloro-2'hydroxy-diphenylether); furan medical preparations like nitrofurantoin and nitrofurazone; methenamine; aldehydes like glutaraldehyde and formaldehyde; and alcohols. In some embodiments, at least one of the antimicrobial agents may be an antiseptic, such as triclosan.

In other embodiments, polymer drugs, i.e., polymeric forms of such compounds, for example, polymeric antibiotics, polymeric antiseptics, polymeric non-steroidal anti-inflammatory drugs (NSAIDS), and the like, may be utilized.

Anionic polymers, including sulfated and/or carboxylated polymers, may be combined with the compositions of the present disclosure. Such anionic polymers may, in embodiments, induce an angiogenic response when implanted in vivo.

In other embodiments, cationically charged particles, such as diethylaminoethyl dextrans (DEAE-dextrans), may be applied. Such particles may increase the rate of healing of cutaneous and other wounds.

In yet other embodiments, quaternary ammonium compounds, which may exert antiseptic properties, may be included.

The compositions of the present disclosure may be combined with various optional ingredients, such as stabilizing agents, thickeners, colors, and the like. The optional ingredients may be present in an amount of up to about 10% of the total weight of the compositions formed with copolymers or blends of the present disclosure.

As low amounts of furanones and/or hydroxamates are required in compositions of the present disclosure, existing formulations and manufacturing processes need only minimal modifications to produce the compositions described herein. This ease of formulation and production may reduce both the time and cost necessary to prepare compositions of the present disclosure, compared with adding other antimicrobial agents or MMP-inhibitors to existing materials.

In embodiments, as the compositions of the present disclosure possess antimicrobial and MMP-inhibiting properties, they may be useful in forming contact lenses, intraocular lenses, and other medical devices or coatings thereon which might otherwise be known to be subject to a high incidence of infection. For contact lenses and intraocular lenses, the lenses may be incubated with a solution which is a poor solvent for the lens, and which possesses the furanone possessing vinyl or acrylate groups, the at least one phospholipid possessing at least one vinyl group, and the hydroxamate. Incubation of the lens with the solution possessing the monomers will swell the surface of the lens with the monomers. The lens and monomers may then be subjected to low dose radiation, such as low dose gamma radiation, to initiate the formation of the copolymer and the graft/interpenetrating polymerization of the copolymer to the lens material.

In other embodiments, compositions of the present disclosure may be utilized as adhesives or sealants. They may also be utilized with other materials to form adhesives or sealants. For example, where methacrylamide units are incorporated into a backbone of a polymer (for example when MPC and NHMAA are combined), the resulting amine groups can be used to crosslink electrophilic groups on other components of an adhesive, for example NHS-functionalized PEGs or polyisocyanate functional components. In other embodiments, two compositions of the present disclosure may be prepared, one with a net positive charge, and the other with a net negative charge: the two compositions may gel upon combination.

As noted above, the compositions of the present disclosure may be utilized to promote wound healing, and may also include immune modulating, neovascularization enhancing/stimulating agents, and additional wound healing agents, to improve wound healing of diseased, injured, and/or compromised tissue in and around a wound. This may be useful in the treatment of many injuries and/or wounds. For example, the compositions of the present disclosure may be useful in the treatment of gastrointestinal anastomoses, either in the formation of implants or coatings thereon, as well as adhesives and/or sealants, to reduce ischemia and/or reperfusion injury, which could lead to a delay in wound healing or tissue necrosis, anastomotic leaks, peritonitis, post-operative adhesions, and potentially death.

In embodiments, a surgical suture, mesh, contact lens, or other medical device may be swollen with a solution containing the furanone possessing vinyl or acrylate groups, the at least one phospholipid possessing at least one vinyl group, and the hydroxamate, optionally in combination with additional vinyl or acrylate monomer. If the device is swollen in a monomer solution utilizing a solvent that does not completely solubilize the monomers, the formation of the resulting copolymer may be localized on the surface of the device and not affect or compromise the bulk properties of the device.

Following polymerization, the device may be removed from the polymerization medium, i.e., the solution containing the monomers and any initiators, catalysts, and the like, and washed to remove excess free copolymer of the present disclosure and/or any residual monomers. The device possessing the copolymer coating, in embodiments grafted and/or interpenetrating, may then be subjected to additional energy treatments, including high energy radiation such as gamma radiation, to both sterilize and further modify the copolymer coating.

In embodiments, a medical device in accordance with the present disclosure may be a suture. Sutures in accordance with the present disclosure may be monofilament or multifilament and may be made of the compositions of the present disclosure or any conventional material, including both bioabsorbable and non-bioabsorbable materials. Suitable materials include, but are not limited to, surgical gut, silk, cotton, polyolefins such as polypropylene, polyamides, polyglycolic acids, polyesters such as polyethylene terephthalate and glycolide-lactide copolymers, and the like.

In embodiments, the suture may be made of a polyolefin. Suitable polyolefins include polyethylene, polypropylene, copolymers of polyethylene and polypropylene, and blends of polyethylene and polypropylene. In some embodiments, polypropylene can be utilized to form the suture. The polypropylene can be isotactic polypropylene or a mixture of isotactic and syndiotactic or atactic polypropylene.

In other embodiments, the suture may be made from synthetic absorbable polymers such as those made from glycolides, lactides, caprolactones, alkylene carbonates (i.e., trimethylene carbonate, tetramethylene carbonate, and the like), dioxanones, orthoesters, hydroxy alkanoates, hydroxybutyrates, tyrosine carbonates, polymide carbonates, polyimino carbonates such as poly(bisphenol A-iminocarbonate) and poly(hydroquinone-iminocarbonate), and copolymers and combinations thereof. One combination which may be utilized includes glycolide and lactide based polyesters, including copolymers of glycolide and lactide.

As noted above, the suture can be monofilament or multifilament. Where the suture is a monofilament, methods for producing such sutures are within the purview of those skilled in the art. Such methods include forming a suture material, such as a polyolefin resin or a copolymer of the present disclosure, and extruding, drawing and annealing the resin of copolymers to form the monofilament.

Where the sutures are made of multiple filaments, the suture can be made using any technique within the purview of one skilled in the art such as, for example, braiding, weaving or knitting. The filaments may also be combined to produce a non-woven suture. The filaments themselves may be drawn, oriented, crinkled, twisted, commingled or air entangled to form yarns as part of the suture forming process.

In embodiments a multifilament suture of the present disclosure can be produced by braiding. The braiding can be done by any method within the purview of those skilled in the art. For example, braid constructions for sutures and other medical devices are described in U.S. Pat. Nos. 5,019,093; 5,059,213; 5,133,738; 5,181,923; 5,226,912; 5,261,886; 5,306,289; 5,318,575; 5,370,031; 5,383,387; 5,662,682; 5,667,528; and 6,203,564, the entire disclosures of each of which are incorporated by reference herein. Once the suture is constructed, it can be sterilized by any means within the purview of those skilled in the art.

In some cases a tubular braid, or sheath, can be constructed about a core structure which is fed through the center of a braider. Known tubular braided sutures, including those possessing cores, are disclosed, for example, in U.S. Pat. Nos. 3,187,752; 3,565,077; 4,014,973; 4,043,344; and 4,047,533.

In embodiments, a suture in accordance with the present disclosure may be attached to any surgical needle within the purview of those skilled in the art to produce a needled suture. Wounds may be sutured by passing a needled suture through tissue to create wound closure. The needle may then be removed from the suture and the suture tied. The suture may remain in the tissue and help prevent contamination and infection of said tissue by virtue of its antimicrobial properties, thereby promoting wound healing and minimizing infection. The suture coating also advantageously enhances the surgeon's ability to pass the suture through tissue, and increases the ease and security with which he/she can tie the suture.

While the above description contains many specifics, these specifics should not be construed as limitations on the scope of the disclosure herein but merely as exemplifications of particularly useful embodiments thereof. Those skilled in the art will envision many other possibilities within the scope and spirit of the disclosure as defined by the claims appended hereto.

What is claimed is:

1. A composition comprising:
    a first component comprising at least one vinyl phospholipid;
    a second component of formula:

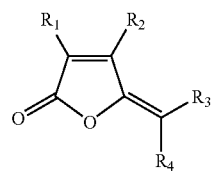

wherein $R_2$, $R_3$ and $R_4$ are independently or all H or halogen; and
    $R_1$ is a moiety selected from the group consisting of H, halogen, formyl, carboxyl, cyano, ester, amide, alkyl, alkoxy, oxoalkyl, alkenyl, alkynyl, aryl or arylalkyl,
    wherein at least one of $R_1$, $R_2$, $R_3$ and $R_4$ are substituted with a moiety selected from the group consisting of vinyl moieties and acrylate moieties; and a third component comprising a hydroxamate of the formula

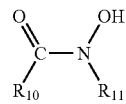

wherein $R_{10}$ is selected from the group consisting of vinyl groups, hydroxy alkyl acrylate groups, hydroxy alkyl methacrylate groups, alkyl amines, acrylamides, methacrylamides, alkyl groups, alkoxy groups, alkenyl groups, polymers terminated with the foregoing groups, and combinations thereof, and $R_{11}$ comprises hydrogen.

2. The composition of claim 1, wherein the first component comprises a phosphorylcholine possessing at least one vinyl group of the formula:

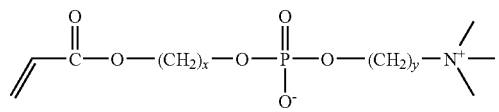

wherein x is from about 1 to about 10, and y is from about 1 to about 10.

3. The composition of claim 1, wherein the first component is selected from the group consisting of 2-methacryloyloxyethyl phosphorylcholine, 2-acryloyloxyethyl phosphorylcholine and combinations thereof.

4. The composition of claim 1, wherein the second component comprises a vinyl furanone.

5. The composition of claim 1, wherein the first component, the second component, and optionally the third component, comprise a copolymer.

6. The composition of claim 5, wherein the copolymer further comprises at least one additional monomer selected from the group consisting of vinyl monomers, acrylate monomers, and combinations thereof.

7. The composition of claim 5, further comprising at least one additional monomer selected from the group consisting of vinyl functional quaternary amines, hydroxyethyl methacrylate, n-vinyl pyrrolidone, sodium acrylate, bis-acrylate, styrene sulfonic acid, butyl acrylate, sulfopropyl acrylate, sulfopropyl methacylate, acrylamide, diacrylamide, methacrylic acid, acrylic acid, polyethylene glycol acrylates, polyethylene glycol/polypropylene glycol acrylates, silicone acrylates, and combinations thereof.

8. A composition comprising:
    a first component comprising a phosphorylcholine possessing at least one vinyl group of the formula:

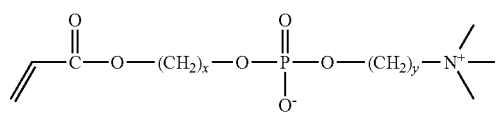

wherein x is from about 1 to about 10 and y is from about 1 to about 10;

a furanone of formula:

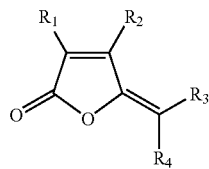

wherein $R_7$, $R_3$ and $R_4$ are independently or all H or halogen, and $R_1$ is a moiety selected from the group consisting of H, halogen, formyl, carboxyl, cyano, ester, amide, alkyl, alkoxy, oxoalkyl, alkenyl, alkynyl, aryl or arylalkyl, wherein at least one of $R_1$, $R_2$, $R_3$ and $R_4$ are substituted with a moiety selected from the group consisting of vinyl moieties and acrylate moieties; and a hydroxamate of the formula:

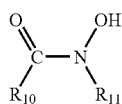

wherein $R_{10}$ is selected from the group consisting of vinyl groups, hydroxy alkyl acrylate groups, hydroxy alkyl methacrylate groups, alkyl amines, acrylamides, methacrylamides, alkyl groups, alkoxy groups, alkenyl groups, polymers terminated with the foregoing groups, and combinations thereof, and $R_{11}$ comprises hydrogen.

9. The composition of claim 8, wherein the first component is selected from the group consisting of 2-methacryloyloxyethyl phosphorylcholine, 2-acryloyloxyethyl phosphorylcholine and combinations thereof.

10. The composition of claim 8, wherein the furanone comprises a vinyl furanone.

11. The composition of claim 8, wherein the first component, the furanone, and optionally the hydroxamate, comprise a copolymer.

12. The composition of claim 11, further comprising at least one additional monomer selected from the group consisting of vinyl monomers, acrylate monomers, and combinations thereof.

13. The composition of claim 11, further comprising at least one additional monomer selected from the group consisting of vinyl functional quaternary amines, hydroxyethyl methacrylate, n-vinyl pyrrolidone, sodium acrylate, bis-acrylate, styrene sulfonic acid, butyl acrylate, sulfopropyl acrylate, sulfopropyl methacylate, acrylamide, diacrylamide, methacrylic acid, acrylic acid, polyethylene glycol acrylates, polyethylene glycol/polypropylene glycol acrylates, silicone acrylates, and combinations thereof.

14. An article comprising:

a first component comprising at least one vinyl phospholipid;

a second component of formula:

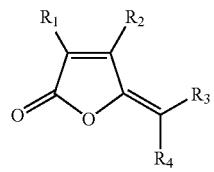

wherein $R_2$, $R_3$ and $R_4$ are independently or all H or halogen; and $R_1$ is a moiety selected from the group consisting of H, halogen, formyl, carboxyl, cyano, ester, amide, alkyl, alkoxy, oxoalkyl, alkenyl, alkynyl, aryl or arylalkyl, wherein at least one of $R_1$, $R_2$, $R_3$ and $R_4$ are substituted with a moiety selected from the group consisting of vinyl moieties and acrylate moieties; and a third component comprising a hydroxamate of the formula:

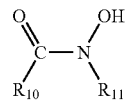

wherein $R_{10}$ is selected from the group consisting of vinyl groups, hydroxy alkyl acrylate groups, hydroxy alkyl methacrylate groups, alkyl amines, acrylamides, methacrylamides, alkyl groups, alkoxy groups, alkenyl groups, polymers terminated with the foregoing groups, and combinations thereof, and $R_{11}$ comprises hydrogen.

15. The article of claim 14, wherein the first component comprises a phosphorylcholine possessing at least one vinyl group of the formula:

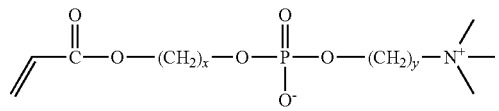

wherein x is from about 1 to about 10, and y is from about 1 to about 10.

16. The article of claim 14, wherein the first component is selected from the group consisting of 2-methacryloyloxyethyl phosphorylcholine, 2-acryloyloxyethyl phosphorylcholine and combinations thereof.

17. The article of claim 14, wherein the second component comprises a vinyl furanone.

18. The article of claim 14, wherein the first component, the second component, and optionally the third component, comprise a copolymer.

19. The article of claim 14, wherein the article is selected from the group consisting of sutures, surgical meshes, contact lenses, intraocular lenses, staples, clips, buttresses, lapbands, catheters, bandages, stents, grafts, stent/grafts, knotless wound closures, sealants, adhesives, anti-adhesion devices, anchors, tunnels, bone fillers, synthetic tendons, synthetic ligaments, grafts, tissue scaffolds, pins, screws, orthopedic hardware, pacers, pacemakers, and implants.

20. A composition comprising:

a first component comprising at least one vinyl phospholipid; and a second component comprising a hydroxamate of the formula:

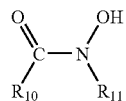

wherein $R_{10}$ is selected from the group consisting of vinyl groups, hydroxy alkyl acrylate groups, hydroxy alkyl methacrylate groups, alkyl amines, acrylamides, methacrylamides, alkyl groups, alkoxy groups, alkenyl groups, polymers terminated with the foregoing groups, and combinations thereof, and $R_{11}$ comprises hydrogen.

* * * * *